(12) United States Patent
Aimin et al.

(10) Patent No.: US 8,390,811 B2
(45) Date of Patent: Mar. 5, 2013

(54) 48-CHANNEL ARRAYED ISOSBESTIC WAVELENGTH DETECTION SYSTEM

(75) Inventors: Yu Aimin, Changchun (CN); Zhende Wang, Changchun (CN)

(73) Assignee: Changchun Jilin University Little Swan Instruments Co., Ltd. (CN)

( * ) Notice: Subject to any disclaimer, the term of this patent is extended or adjusted under 35 U.S.C. 154(b) by 233 days.

(21) Appl. No.: 13/056,898

(22) PCT Filed: Dec. 9, 2009

(86) PCT No.: PCT/CN2009/001394
§ 371 (c)(1),
(2), (4) Date: Jan. 31, 2011

(87) PCT Pub. No.: WO2011/011908
PCT Pub. Date: Feb. 3, 2011

(65) Prior Publication Data
US 2011/0134425 A1  Jun. 9, 2011

(30) Foreign Application Priority Data
Jul. 31, 2009  (CN) .......................... 2009 1 0090182

(51) Int. Cl.
*G01N 21/00* (2006.01)
(52) U.S. Cl. ...................................... 356/432
(58) Field of Classification Search .................. None
See application file for complete search history.

(56) References Cited

U.S. PATENT DOCUMENTS

| | | | |
|---|---|---|---|
| 5,408,326 A | 4/1995 | Wang | |
| 6,411,835 B1 * | 6/2002 | Modell et al. | 600/407 |
| 2003/0139886 A1 * | 7/2003 | Bodzin et al. | 702/28 |
| 2005/0079627 A1 | 4/2005 | Jones et al. | |

FOREIGN PATENT DOCUMENTS

| | | |
|---|---|---|
| CN | 1336157 A | 2/2002 |
| CN | 201096718 Y | 8/2008 |
| CN | 201166659 Y | 12/2008 |
| CN | 101988893 B | 3/2011 |
| JP | 2000-230906 A | 8/2000 |
| JP | 2003057192 A | 2/2003 |
| WO | 01/02839 A1 | 1/2001 |
| WO | 01/92870 A2 | 12/2001 |

OTHER PUBLICATIONS

International Search Report in corresponding Patent Application No. PCT/CN2009/001394, dated May 13, 2010, 5 pages.
International Preliminary Report on Patentability in corresponding International Patent Application No. PCT/CN2009/001394, dated Jan. 31, 2012, 5 pages.
Document Including English Translation Abstracts of Foreign Patent Documents Cites 3, 4, 6, 7 and 8.

* cited by examiner

*Primary Examiner* — Tu Nguyen
(74) *Attorney, Agent, or Firm* — Pedigo Law Firm, PLLC

(57) ABSTRACT

A multi-channel arrayed isosbestic wavelength detection system comprises an arrayed light source board, an arrayed photoelectric sensor board, and an intermediate system frame. The arrayed light source board and arrayed photoelectric sensor board are assembled at opposite sides of the intermediate system frame. In addition, the arrayed light source system has a plurality of light-emitting elements, each of which comprises two monochromatic light sources that provide main wavelength and reference wavelength respectively, and the two wavelengths are isosbestic wavelengths. The arrayed photoelectric sensor system has a plurality of photoelectric sensors, which are aligned at fixed positions in one-to-one correspondence with the light-emitting elements.

20 Claims, 4 Drawing Sheets

48-CHANNEL ARRAYED ISOSBESTIC WAVELENGTH DETECTION SYSTEM

TECHNICAL FIELD

The invention pertains to the technical field of photometric analysis, and particularly relates to a multi-channel arrayed isosbestic wavelength detection system for use in a photometric analyzer.

BACKGROUND ART

Photometry is a material concentration analysis method established on the basis of selective light absorption of materials, and is one of popular instrumental analysis methods at present. The theoretical foundation of photometry is the Lamber-Beer Law. Most existing photometric analyzers employ a single-wavelength and single-channel detection system. Owing to the technical characteristics of photometry, single-wavelength photometric detection may be affected by the noise, drifting, and contamination of the instrument, causing errors in the detection result. In addition, in a single-channel detection system, the cuvette or light source has to be replaced in the operation to obtain acceptable detection result. Therefore, such a system has drawbacks such as complex operation and troublesome switching, and can't meet the demand for accurate, rapid, and efficient detection.

SUMMARY OF THE INVENTION

The object of the invention is to provide a simple, sensitive, and quick 48-channel arrayed isosbestic wavelength detection system, to meet the demand for accurate, rapid, and efficient detection.

To attain the above object, the invention puts forward a 48-channel arrayed isosbestic wavelength detection system, comprising an arrayed light source board and an arrayed photoelectric sensor board, wherein, the arrayed light source board and arrayed photoelectric sensor board are assembled at opposite sides of an intermediate system frame; the arrayed light source board has a plurality of light-emitting elements aligned in an array, and each light-emitting element comprises two monochromatic light sources that provide main wavelength and reference wavelength respectively, and the wavelengths provided by the two monochromatic light sources in the same light-emitting element are isosbestic wavelengths; the arrayed photoelectric sensor board has a plurality of photoelectric sensors; in addition, the light-emitting elements are aligned at fixed positions in one-to-one correspondence with the photoelectric sensors.

In the 48-channel arrayed isosbestic wavelength detection system, the arrayed light source board comprises a light source mainboard and a light source base; the light source base is arranged between the intermediate system frame and the light source mainboard; monochromatic light sources are arranged on the light source mainboard, and control circuits and a circuit connector designed to connect electrically to the single-chip microprocessor in a photometric analyzer are distributed on the light source mainboard; the light source base has a plurality of bottom holes that match the monochromatic light sources.

In the 48-channel arrayed isosbestic wavelength detection system, the arrayed photoelectric sensor board comprises a photoelectric sensor mainboard and a photoelectric sensor base; the photoelectric sensor base is arranged between the intermediate system frame and the photoelectric sensor mainboard; photoelectric sensors are arranged on the photoelectric sensor mainboard, and control circuits and a circuit connector designed to connect electrically to the single-chip microprocessor in a photometric analyzer are distributed on the photoelectric sensor mainboard; the photoelectric sensor base has a plurality of bottom holes that match the photoelectric sensors.

In the 48-channel arrayed isosbestic wavelength detection system, connecting holes are arranged at positions corresponding to each other on the arrayed light source board, arrayed photoelectric sensor board, and intermediate system frame, and the arrayed light source board, arrayed photoelectric sensor board, and intermediate system frame are connected together by fastening bolts through the connecting holes.

In the 48-channel arrayed isosbestic wavelength detection system, the wavelengths of monochromatic light sources can be different between different light-emitting elements.

In the 48-channel arrayed isosbestic wavelength detection system, the intermediate system frame comprises a supporting frame, which has internal dimensions matching the dimensions of the cuvettes loaded in the detection system.

In the 48-channel arrayed isosbestic wavelength detection system, the monochromatic light sources can be ultra high brightness light emitting diodes (LEDs) that emit homogeneous monochromatic light.

The invention further puts forward a multi-channel arrayed isosbestic wavelength photometric analysis method, in which the 48-channel arrayed isosbestic wavelength detection system described above is utilized in a spectrophotometer, and cuvettes containing samples to be tested are loaded into the supporting frame of the intermediate frame.

In the photometric analysis method, the same sample is loaded into different cuvettes, each of which corresponds to a light-emitting element that emits light in isosbestic wavelength, so as to detect several parameters of the same sample.

In the photometric analysis method, different samples are loaded into different cuvettes, each of which corresponds to a light-emitting element that emits light in isosbestic wavelength, so as to detect the same parameter among different samples.

The above described technical scheme employed by the invention has the following advantages:

1. A dual-wavelength photometric method is employed, so as to improve the accuracy of the detection result.
2. The light sources in each detection channel provide a main wavelength and a reference wavelength, and the main wavelength and reference wavelength in the same detection channel are isosbestic wavelengths, and correspond to the same photoelectric sensor.
3. Arrayed light sources assembled from ultra high brightness LEDs are employed, featuring long service life (100,000 hours), quick response, and free of pollution to the environment.
4. Since the light-emitting elements in the light sources are aligned at fixed positions in one-to-one correspondence with the corresponding photoelectric sensors; since there is no moving part in the detection process, and therefore the detection result is more stable; thus, the method is highly practical.

DETAILED DESCRIPTION OF THE EMBODIMENTS

Hereunder the embodiments of the invention will be described, with reference to the accompanying drawings.

The invention provides a special detection system for photometric analyzer, which is in multi-channel and dual-wavelength design. At present, common photometric analyzers usually comprise a cuvette, a detection system, a single-chip microprocessor, and a power supply unit. Wherein, the cuvette contains the sample to be tested, the single-chip microprocessor controls the detection system and processes the detection result, and the power supply unit supplies power to active parts; the detection system usually comprises a light source and a detector, and is used to test the sample, wherein, the light source provides light in specific wavelength required for the detection, the detector transforms the light transmitted through the tested sample into electric signals. The main working principle of such a photometric analyzer is essentially the same as that shown in FIG. 7.

The system in accordance with the invention is a multi-channel detection system, in which appropriate main wavelength and reference wavelength can be set in advance in different detection channels for different samples to be tested, so that it is unnecessary to replace the light source frequently in the operation. As a result, the detection procedures are simplified, and the practicability of the detection system is improved.

The invention mainly improves the detection system used in photometric analyzer. In the invention, a dual-wavelength photometric method is used to overcome the drawbacks of single-wavelength detection. The dual-wavelength photometric method is based on the theoretical basis of differential absorbance and isosbestic wavelength. For materials that have absorption peaks in their absorption spectrum, isosbestic wavelengths refer to two wavelengths with the same absorbance at the same material concentration. Compared to the conventional single-wavelength photometric method, the difference of dual-wavelength photometric method lies in: two wavelengths are employed at the same time to detect the same solution, and the difference between absorbance values detected at the two wavelengths is proportional to the concentration of the tested solution. With dual-wavelength photometric method, the detection result is not affected by factors such as noise, drifting, or contamination of the instrument, and therefore the accuracy of detection result can be improved.

Figure 1:
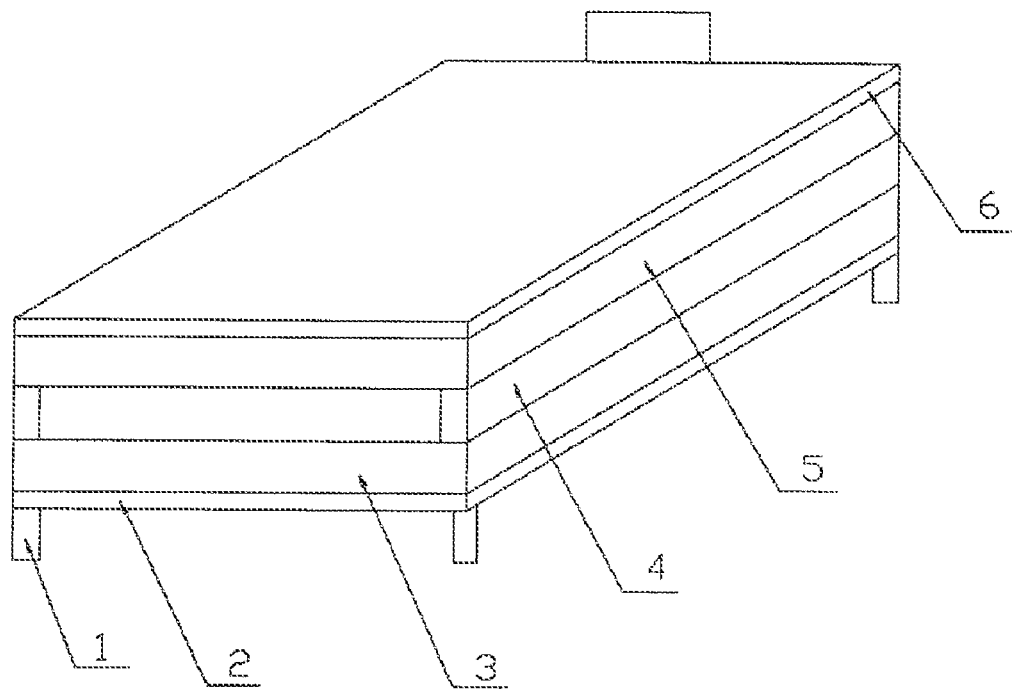
FIG. 1 is a schematic structural diagram of the 48-channel arrayed isosbestic wavelength detection system in accordance with the invention.

The structure of the detection system in accordance with the invention is shown in FIG. 1. The detection system comprises an intermediate system frame 4, a light source base 3 arranged under the intermediate system frame 4, and a photoelectric sensor base 5 arranged on the intermediate system frame 4. Wherein, a light source mainboard 2 is arranged under the light source base 3, and a photoelectric sensor mainboard 6 is arranged on the photoelectric sensor base 5. In addition, the intermediate system frame 4 secures the light source base 3 and the photoelectric sensor base 5 tightly with fastening bolts 1.

Figure 2:
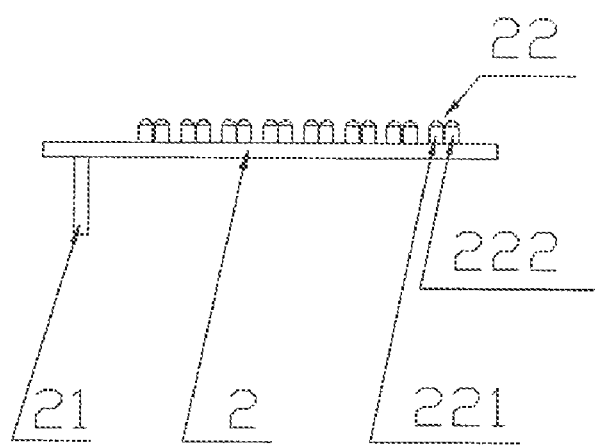
FIG. 2 is a schematic structural diagram of the light source mainboard in the 48-channel arrayed isosbestic wavelength detection system in accordance with the invention.

The structure of the light source mainboard 2 is shown in FIG. 2. Control circuits (see FIG. 8A for the schematic diagram of the control circuits) and a connector 21 for the light source mainboard are distributed on one side of the light source mainboard 2; the control circuits are electrically connected to the single-chip microprocessor in a photometric analyzer via the connector 21, so as to receive control instructions from the single-chip microprocessor. A light source system is arranged on the other side of the light source mainboard 2. The light source system has a plurality of light-emitting elements 22, each of which comprises a primary wavelength LED 221 and a secondary wavelength LED 222. The primary wavelength LED 221 provides main wavelength, while the secondary wavelength LED 222 provides reference wavelength, and the main wavelength and reference wavelength are isosbestic wavelengths. The light-emitting elements 22 can be aligned into an array; for example, 48 light-emitting elements composed of 96 ultra high brightness LEDs can be distributed evenly on the light source mainboard 2 to form an array. The light source mainboard 2 can be a standard PCB.

Figure 3:
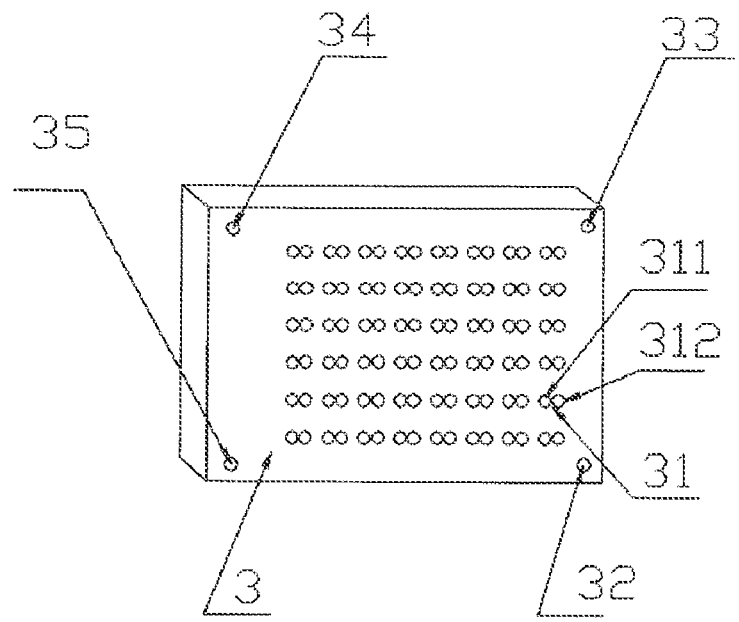
FIG. 3 is a schematic structural diagram of the light source base in the 48-channel arrayed isosbestic wavelength detection system in accordance with the invention.

The structure of the light source base 3 is shown in FIG. 3. The light source base 3 is made of aluminum alloy material, and has distributed thereon a plurality of LED bottom hole groups 31. Each LED bottom hole group 31 comprises a bottom hole 311 that corresponds to the primary wavelength LED and a bottom hole 312 that corresponds to the secondary wavelength LED. The bottom holes that correspond to the LEDs are through-holes, and their dimensions and alignment match the dimensions and alignment of the LEDs on the light source mainboard 2. Connecting holes 32, 33, 34, and 35 for light source system are arranged at the four top corners of the light source base 3; the light source base, photoelectric sensor base, and intermediate system frame are secured together by fastening bolts 1 through these connecting holes.

Of course, on the basis of above description, the light source mainboard 2 and the light source base 3 can be embodied as a single piece of arrayed light source board.

Figure 6:
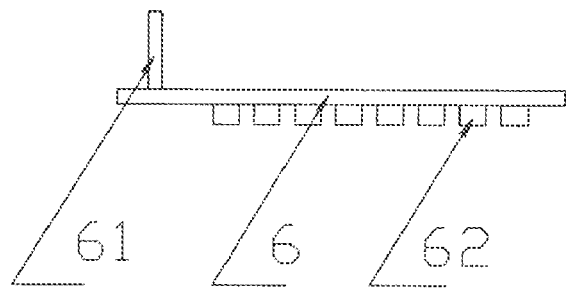
FIG. 6 is a schematic structural diagram of the photoelectric sensor mainboard in the 48-channel arrayed isosbestic wavelength detection system in accordance with the invention.

The structure of the photoelectric sensor mainboard 6 is shown in FIG. 6. Control circuits (see FIG. 8B for the schematic diagram of the control circuits) and a connector 61 for photoelectric sensor mainboard are distributed on one side of the photoelectric sensor mainboard 6; the control circuits are electrically connected to the single-chip microprocessor in a photometric analyzer via the connector 61, so as to transmit the detection signals received by the photoelectric sensors to the single-chip microprocessor for analysis and processing. A plurality of photoelectric sensors 62 are arranged on the other side of the photoelectric sensor mainboard 6, and are in the same quantity as the light-emitting elements 22 on the main light source board; in addition, the positions and alignment of the photoelectric sensors 62 match the positions and alignment of the light-emitting elements 22 on the light source mainboard; for example, if there are 48 light-emitting elements (i.e., there are 96 LEDs), 48 photoelectric sensors 62 are arranged; in addition, the positions and alignment of the photoelectric sensors 62 match the positions and alignment of the corresponding light-emitting elements 22. The photoelectric sensor mainboard 6 can be a standard PCB.

Figure 5:
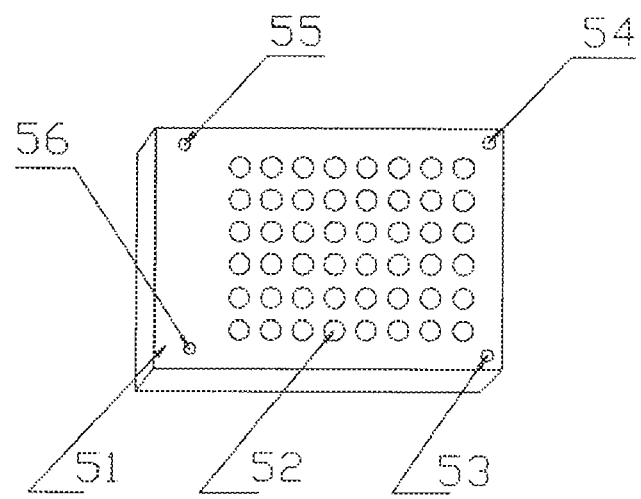
FIG. 5 is a schematic structural diagram of the photoelectric sensor base in the 48-channel arrayed isosbestic wavelength detection system in accordance with the invention.

The structure of the photoelectric sensor base 5 is shown in FIG. 5. The photoelectric sensor base 5 has a photoelectric sensor backboard 51 made of aluminum alloy material and having photoelectric sensor bottom holes 52 distributed thereon evenly in an array. The photoelectric sensor bottom holes 52 are through-holes, and their dimensions and alignment match the dimensions and alignment of the photoelectric sensors 62 on the photoelectric sensor mainboard 6. Connecting holes 53, 54, 55 and 56 for photoelectric sensor system are arranged at the four top corners of the photoelectric sensor base; the light source base, photoelectric sensor base, and intermediate system frame are secured together by fastening bolts 1 through these connecting holes.

Of course, on the basis of above description, the photoelectric sensor mainboard 6 and the photoelectric sensor base 5 can be embodied as a single piece of arrayed photoelectric sensor board.

Figure 4:
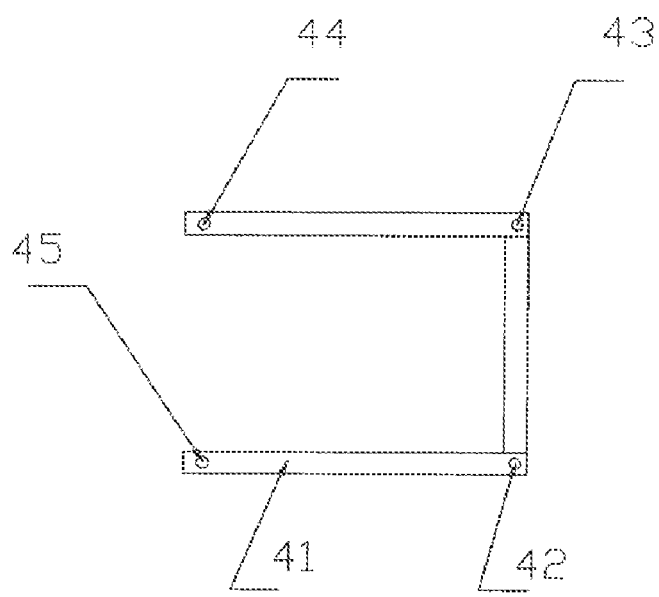
FIG. 4 is a schematic structural diagram of the intermediate system frame in the 48-channel arrayed isosbestic wavelength detection system in accordance with the invention.

The structure of the intermediate system frame 4 is shown in FIG. 4. The intermediate system frame 4 is made of aluminum alloy material, and comprises a supporting frame 41; the internal dimensions of the supporting frame 41 match the dimensions of the cuvettes loaded in the detector system. As shown in FIG. 4, connecting holes 42, 43, 44, and 45 for intermediate system frame are arranged on the intermediate system frame, at positions corresponding to the connecting holes for light source system and connecting holes for photoelectric sensor system; the light source base, photoelectric sensor base, and intermediate system frame are secured together by fastening bolts 1 through these connecting holes for intermediate system frame. During sample test, cuvettes are inserted into the intermediate system frame 4. The cuvettes are ELISA plates or cell culture plates. Specifically, they work with the isosbestic wavelengths provided by the light-emitting elements. The cuvettes will not be further detailed here.

As described above, the light-emitting elements, LED bottom hole groups, photoelectric sensor bottom holes, and photoelectric sensors are in one-to-one correspondence with each other. Each light-emitting element together with corresponding LED bottom hole group, cuvette in the intermediate system frame, photoelectric sensor bottom hole, and photoelectric sensor form a detection channel. For example, in this embodiment, with 48 light-emitting elements 22, the detection system provides 48 detection channels.

Figure 7:
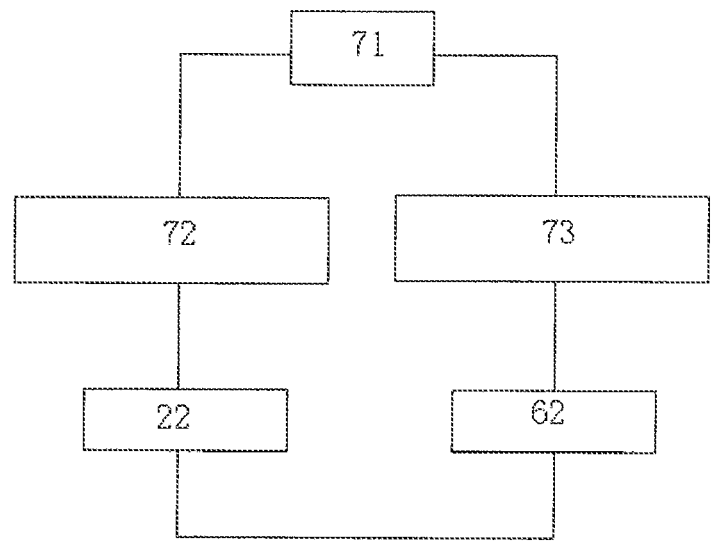
FIG. 7 is a schematic diagram of working principle illustrating how the detection system in accordance with the invention can be applied into photometric analyzer.

The working principle illustrating how the detection system in accordance with the invention can be applied in a photometric analyzer is shown in FIG. 7: according to the functional requirements, the single-chip microprocessor 71 in the photometric analyzer sends control instructions to a control circuit 72 on the light source mainboard; the control circuit 72 controls the light-emitting element 22 to emit light under the control instructions from the single-chip microprocessor 71; the light emitted from the light-emitting element 22 is absorbed by the tested sample in the cuvette and then transmitted into the photoelectric sensor 62; the photoelectric sensor 62 converts the received optical signals into electric signals, and sends the electric signals through the control circuit 73 on the photoelectric sensor mainboard to the single-chip microprocessor 71 for analysis and processing.

Figure 8A:
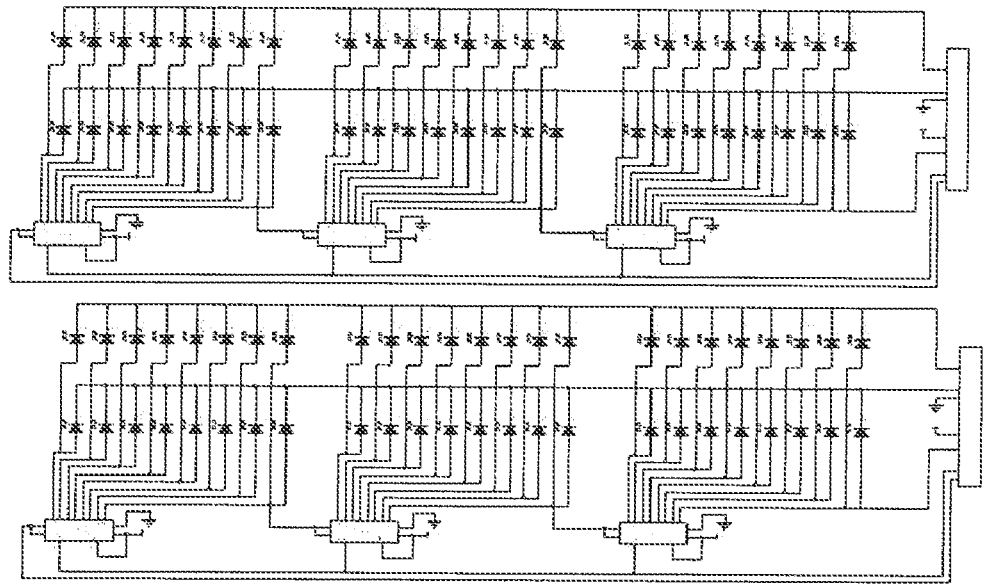
FIG. 8A is a schematic circuit diagram of the light source mainboard in the 48-channel arrayed isosbestic wavelength detection system in accordance with the invention.
Figure 8B:
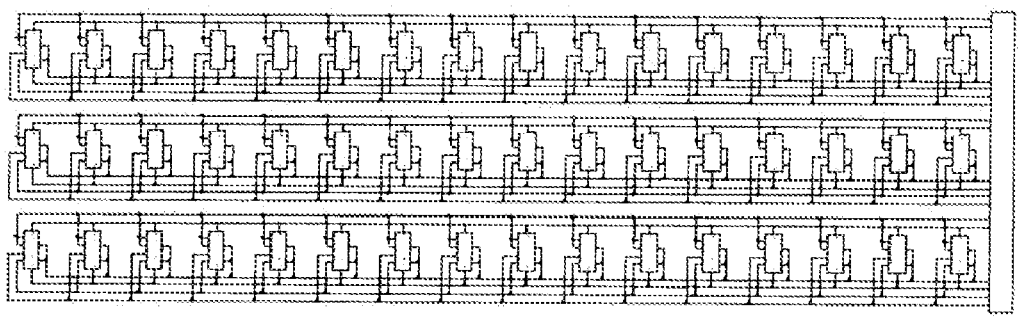
FIG. 8B is a schematic circuit diagram of the photoelectric sensor mainboard in the 48-channel arrayed isosbestic wavelength detection system in accordance with the invention.

In this embodiment, the working principle of light source mainboard, working principle of photoelectric sensor mainboard, and relevant circuit connections in the 48-channel arrayed isosbestic wavelength detection system can be known with reference to FIG. 8A and FIG. 8B; the circuit connections are only a specific type of circuit connections designed to implement the fore-mentioned function, and shall not be deemed as constituting any limitation excluding other types of possible circuit connections.

In this embodiment, ultra high brightness LEDs produced by Nichia (Japan) and Toyota (Japan), with luminance higher than 5000 mcd, are employed for the monochromatic light sources; integrated photoelectric sensors produced by TI (USA) are employed for the photoelectric sensors. Of course, other equivalent monochromatic light sources and integrated photoelectric sensors can also be used in the invention.

Hereunder by means of a specific example, an introduction will be made as to how the 48-channel arrayed isosbestic wavelength detection system in accordance with the invention can be utilized in a photometric analyzer.

The detection of chemical oxygen demand in water is described herein as an example. The 48-channel arrayed isosbestic wavelength detection system in accordance with the invention was designed into a 48-channel arrayed isosbestic wavelength chemical oxygen demand detector. The main wavelength was designed as 614 nm, and the reference wavelength was designed as 680 nm, depending on the reagent used in the experiment.

The tested sample was a solution composed of water sample, and reference material CBW (E) 080273 certified by National Research Center for Certified Reference Materials, and the concentration of the reference material in the solution was 30 mg/l. The water sample and the reference material were prepared as a solution in accordance with pretreatment method for chemical oxygen demand test.

Color development measurement operation: the operation was performed as prompted by the instrument, to obtain the measurement results of relevant components in the sample.

According to the general principles for chemical experiments, 11 groups of samples were tested in parallel in this experiment.

Under the same conditions, the samples were detected with a conventional chemical oxygen demand detector (single channel, 614 nm wavelength).

Comparison of results: when the concentration of the reference material was 30 mg/l, the comparison between the two data sets was shown in Table 1.

As indicated in the experiment data in Table 1, the relative standard deviation in the detection result obtained with dual-wavelength method was much better than that in the detection result obtained with single-wavelength method.

TABLE 1

Detection Results of Chemical Oxygen Demand Obtained with Single-Wavelength Method and Dual-Wavelength Method (Concentration: mg/l)

| Type | Group 1 | Group 2 | Group 3 | Group 4 | Group 5 | Group 6 | Group 7 | Group 8 | Group 9 | Group 10 | Group 11 | Average | Standard Deviation | Relative Standard Deviation |
|---|---|---|---|---|---|---|---|---|---|---|---|---|---|---|
| Single-wavelength | 33 | 31 | 34 | 32 | 27 | 29 | 30 | 31 | 29 | 28 | 31 | 30.5 | 2.02 | 6.62 |
| Dual-wavelength | 31 | 30 | 29 | 31 | 30 | 30 | 30 | 29 | 31 | 30 | 29 | 30.0 | 0.74 | 2.46 |

INDUSTRIAL APPLICABILITY

In the 48-channel arrayed isosbestic wavelength detection system in accordance with the invention, a dual-wavelength photometric method is used, the light source in each detection channel provides a main wavelength and a reference wavelength, and the main wavelength and reference wavelength in the same detection channel are isosbestic wavelengths, and correspond to the same photoelectric sensor; therefore, the accuracy of detection result is improved; in addition, the light-emitting elements in the light source are aligned at fixed positions in one-to-one correspondence with the corresponding photoelectric sensors; since there is no moving part in the detection process, the detection result is more stable, and the system is more practical, and can meet the demand for accurate, quick, and efficient detection.

The invention claimed is:

1. A multi-channel arrayed isosbestic wavelength detection system, comprising an arrayed light source board and an arrayed photoelectric sensor board, wherein:
    the arrayed light source board and arrayed photoelectric sensor board are assembled at opposite sides of an intermediate system frame;
    a plurality of light-emitting elements aligned in an array are arranged on the arrayed light source board, and each light-emitting element comprises two monochromatic light sources that provide main wavelength and reference wavelengths respectively, and the wavelengths provided by the two monochromatic light sources in the same light-emitting element are isosbestic wavelengths; and
    a plurality of photoelectric sensors are arranged on the arrayed photoelectric sensor board, and the light-emitting elements are aligned at fixed positions in one-to-one correspondence with the photoelectric sensors.

2. The multi-channel arrayed isosbestic wavelength detection system according to claim 1, wherein the arrayed light source board comprises a light source mainboard and a light source base, and the light source base is arranged between the intermediate system frame and the light source mainboard;
    the monochromatic light sources are arranged on the light source mainboard, and control circuits and a circuit connector designed to connect electrically to the single-chip microprocessor in a photometric analyzer are distributed on the light source mainboard; and
    a plurality of bottom holes that match the monochromatic light sources are arranged on the light source base.

3. The multi-channel arrayed isosbestic wavelength detection system according to claim 2, wherein: the arrayed photoelectric sensor board comprises a photoelectric sensor mainboard and a photoelectric sensor base, and the photoelectric sensor base is arranged between the intermediate system frame and the photoelectric sensor mainboard;
    the photoelectric sensors are arranged on the photoelectric sensor mainboard, and control circuits and a circuit connector designed to connect electrically to the single-chip microprocessor in a photometric analyzer are distributed on the photoelectric sensor mainboard; and
    a plurality of bottom holes that match the photoelectric sensors are arranged on the photoelectric sensor base.

4. A multi-channel arrayed isosbestic wavelength photometric analysis method, in which the multi-channel arrayed isosbestic wavelength detection system as claimed in claim 3 is employed in a spectrophotometer, and cuvettes containing the tested samples are loaded into the supporting frame of the intermediate system frame.

5. The photometric analysis method according to claim 4, wherein, the same sample is loaded into different cuvettes, with each cuvette corresponding to a light-emitting element that emits light in an isosbestic wavelength, so as to detect several parameters of the same sample.

6. The photometric analysis method according to claim 4, wherein, different samples are loaded into different cuvettes, with each cuvette corresponding to a light-emitting element that emits light in an isosbestic wavelength, so as to detect the same parameter among different samples.

7. A multi-channel arrayed isosbestic wavelength photometric analysis method, in which the multi-channel arrayed isosbestic wavelength detection system as claimed in claim 2 is employed in a spectrophotometer, and cuvettes containing the tested samples are loaded into the supporting frame of the intermediate system frame.

8. The multi-channel arrayed isosbestic wavelength detection system according to claim 1, wherein: the arrayed photoelectric sensor board comprises a photoelectric sensor mainboard and a photoelectric sensor base, and the photoelectric sensor base is arranged between the intermediate system frame and the photoelectric sensor mainboard;
    the photoelectric sensors are arranged on the photoelectric sensor mainboard, and control circuits and a circuit connector designed to connect electrically to the single-chip microprocessor in a photometric analyzer are distributed on the photoelectric sensor mainboard; and
    a plurality of bottom holes that match the photoelectric sensors are arranged on the photoelectric sensor base.

9. A multi-channel arrayed isosbestic wavelength photometric analysis method, in which the multi-channel arrayed isosbestic wavelength detection system as claimed in claim 8 is employed in a spectrophotometer, and cuvettes containing the tested samples are loaded into the supporting frame of the intermediate system frame.

10. The multi-channel arrayed isosbestic wavelength detection system according to claim 1, wherein:
    connecting holes are arranged at positions corresponding to each other on the arrayed light source board, arrayed photoelectric sensor board, and intermediate system frame, and the arrayed light source board, arrayed photoelectric sensor board, and intermediate system frame are connected together by fastening bolts through the connecting holes.

11. The multi-channel arrayed isosbestic wavelength detection system according to claim 1, wherein, the wavelengths of monochromatic light source are different between different light-emitting elements.

12. A multi-channel arrayed isosbestic wavelength photometric analysis method, in which the multi-channel arrayed isosbestic wavelength detection system as claimed in claim 11 is employed in a spectrophotometer, and cuvettes containing the tested samples are loaded into the supporting frame of the intermediate system frame.

13. The photometric analysis method according to claim 12, wherein, the same sample is loaded into different cuvettes, with each cuvette corresponding to a light-emitting element that emits light in an isosbestic wavelength, so as to detect several parameters of the same sample.

14. The multi-channel arrayed isosbestic wavelength detection system according to claim 1, wherein, the intermediate system frame comprises a supporting frame, which has internal dimensions matching the dimensions of the cuvettes loaded in the detection system.

15. The multi-channel arrayed isosbestic wavelength detection system according to claim 1, wherein, the monochromatic light sources are ultra high brightness LEDs that emit homogeneous monochromatic light.

16. A multi-channel arrayed isosbestic wavelength photometric analysis method, in which the multi-channel arrayed isosbestic wavelength detection system as claimed in claim 15 is employed in a spectrophotometer, and cuvettes containing the tested samples are loaded into the supporting frame of the intermediate system frame.

17. The photometric analysis method according to claim 16, wherein, different samples are loaded into different cuvettes, with each cuvette corresponding to a light-emitting element that emits light in an isosbestic wavelength, so as to detect the same parameter among different samples.

18. A multi-channel arrayed isosbestic wavelength photometric analysis method, in which the multi-channel arrayed isosbestic wavelength detection system as claimed in claim 1 is employed in a spectrophotometer, and cuvettes containing the tested samples are loaded into the supporting frame of the intermediate system frame.

19. The photometric analysis method according to claim 18, wherein, the same sample is loaded into different cuvettes, with each cuvette corresponding to a light-emitting element that emits light in an isosbestic wavelength, so as to detect several parameters of the same sample.

20. The photometric analysis method according to claim 18, wherein, different samples are loaded into different cuvettes, with each cuvette corresponding to a light-emitting element that emits light in an isosbestic wavelength, so as to detect the same parameter among different samples.

* * * * *